(12) United States Patent
Bichler et al.

(10) Patent No.: US 10,098,775 B2
(45) Date of Patent: Oct. 16, 2018

(54) DEVICE FOR STABILIZING BODY JOINTS, MUSCLES AND TENDONS

(71) Applicant: Betterguards Technology GmbH, Berlin (DE)

(72) Inventors: Vinzenz Bichler, Berlin (DE); Timo Stumper, Berlin (DE)

(73) Assignee: Betterguards Technology GmbH, Berlin (DE)

( * ) Notice: Subject to any disclaimer, the term of this patent is extended or adjusted under 35 U.S.C. 154(b) by 386 days.

(21) Appl. No.: 15/095,035

(22) Filed: Apr. 9, 2016

(65) Prior Publication Data

US 2016/0331569 A1 Nov. 17, 2016

(30) Foreign Application Priority Data

May 12, 2015 (DE) .................. 10 2015 107 408

(51) Int. Cl.
*A61F 5/01* (2006.01)
*F16F 9/20* (2006.01)

(52) U.S. Cl.
CPC .......... *A61F 5/0104* (2013.01); *A61F 5/0111* (2013.01); *F16F 9/20* (2013.01); *A61F 2005/0169* (2013.01); *A61F 2005/0197* (2013.01); *F16F 2224/041* (2013.01)

(58) Field of Classification Search
CPC .............. A61F 5/0104; A61F 5/0111; A61F 2005/0169; A61F 2005/0197; A61F 5/0127; A61F 5/0585; A61F 5/0113; A61F 5/0102; A61F 5/05816; A61F 5/012; A61F 5/028; A61F 5/34; F16F 9/20; F16F 2224/041; A43B 7/20; A61H 9/0078
See application file for complete search history.

(56) References Cited

U.S. PATENT DOCUMENTS

| 4,471,538 A | 9/1984 | Pomeranz et al. |
|---|---|---|
| 5,450,931 A | 9/1995 | Masuda et al. |
| 5,712,011 A | 1/1998 | McMahon et al. |
| 2014/0015176 A1 | 1/2014 | Wetzel et al. |

FOREIGN PATENT DOCUMENTS

| DE | 10 2014 107 335 A1 | 1/2016 |
|---|---|---|
| WO | 94/12066 A1 | 6/1994 |
| WO | 2013/174989 A1 | 11/2013 |
| WO | WO 2013/174989 A1 | 11/2013 |

*Primary Examiner* — Ophelia A Hawthorne
(74) *Attorney, Agent, or Firm* — Bookoff McAndrews, PLLC

(57) ABSTRACT

A device includes a receptacle body, wherein the receptacle body is filled with a dilatant fluid and the receptacle body extends in an elongated shape from a first end towards a second end, and a tension body for initiating an external force into the device, wherein a compression body, wherein the compression body is arranged in the receptacle body in a relatively movable manner and is connected to the tension body, wherein the compression body divides an interior space of the receptacle body into a first chamber and a second chamber, wherein between the receptacle body and the compression body a passage is provided, wherein the passage connects the first chamber with the second chamber fluid-technically.

17 Claims, 15 Drawing Sheets

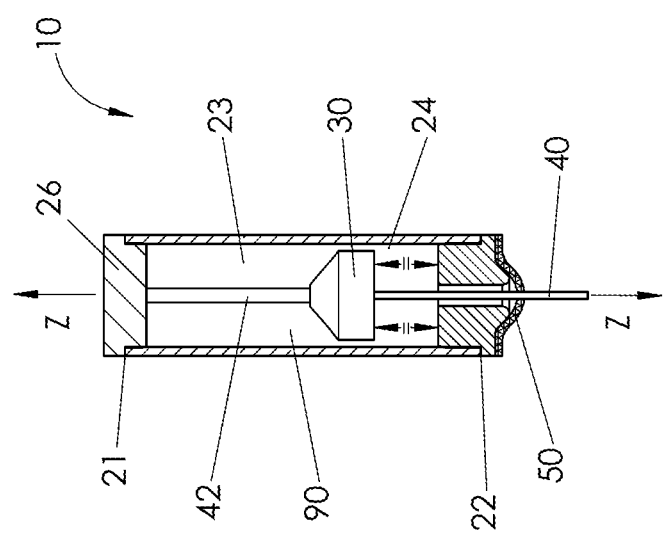

A-A

B-B

DEVICE FOR STABILIZING BODY JOINTS, MUSCLES AND TENDONS

CROSS-REFERENCE TO RELATED APPLICATION(S)

This application claims priority to German Patent Application No. DE 10 2015 107 408.7, filed on May 12, 2015, the entirety of which is incorporated herein by reference.

TECHNICAL FIELD

The present invention relates to a device for stabilizing body joints, muscles and tendons comprising a receptacle body, wherein the receptacle body is filled with a dilatant fluid and the receptacle body extends in an elongated shape from a first end towards a second end, and a tension body for initiating an external force into the device.

PRIOR ART

It is known to stabilize body joints, muscles and tendons by means of devices which permit an adaptive motion limiting. Inter alia, the adaptive behavior of such devices is achieved by two bodies moving relative to each other, wherein there is a dilatant fluid between the bodies. The opposing surfaces of the bodies form shear surfaces that initiate shear forces into the dilatant fluid due to the relative motion. The greater the shear forces are the more viscous the dilatant fluid behaves. From a defined shear force, the dilatant fluid experiences a shear step, through which the degree of consolidation increases rapidly.

The devices can be fixed between two parts of the body of a user. Thereby, one shear body of the device forms a receptacle which is filled with the dilatant fluid. The other shear body forms a pull-out-body which is movably arranged in the receptacle. If physiological forces, i.e., forces uncritical for the corresponding body part that is to be stabilized, are introduced into the device via the two parts of the body of the user, then, due to the liquid state of the dilatant fluid, a relative movement of the receptacle and the pull-out-body and thus a movement of the body part that is to be stabilized is admitted.

If, however, non-physiological forces, i.e., forces critical for the corresponding body part that is to be stabilized, are introduced into the device, the shear forces emanating from the shearing surfaces of the receptacle and the pull-out-body cause a shear hardening of dilatant fluid, through which a relative movement between the pull-out-body and the receptacle is no longer possible.

Such a device is known for example from WO 2013/174989 A1, which shows an orthopaedic device for limiting the movement of a joint arranged between a first and a second region of a body.

Since the mode of action of such devices is based on the shear between the receptacle and the pull-out-body, the size of the shearing surfaces is decisive. The greater the forces are that usually appear on the body part to be stabilized, the greater the shearing surfaces of the device have to be designed.

However, large opposing surfaces of the receptacle and the pull-out-body require larger space. Especially in sports, where the occurrence of high forces is common, devices with large dimensions are impractical. Devices protruding from the body surface may impede the user and third parties.

SUMMARY OF THE INVENTION

Starting from the known state of the art, it is an object of the present invention to provide an improved apparatus for the stabilization of body joints, muscles and tendons.

This object is achieved by means of a device having the features of claim 1. Advantageous embodiments can be taken from the dependent claims.

Accordingly, a device for stabilizing body joints, muscles and tendons is given that comprises a receptacle body, wherein the receptacle body is filled with a dilatant fluid and the receptacle body extends in an elongated shape from a first end towards a second end, and a tension body for initiating an external force into the device. According to the invention the device comprises a compression body, which is arranged in the receptacle body in a relatively movable manner and is connected to the tension body, wherein the compression body divides an interior space of the receptacle body into a first chamber and a second chamber, wherein between the receptacle body and the compression body a passage is provided, wherein the passage connects the first chamber with the second chamber fluid-technically, and wherein the compression body comprises at least one compression surface which substantially defines one side of the second chamber, wherein the compression surface can press onto the dilatant fluid situated in the second chamber.

This enables an adaptive limitation of movement, which is based on the shear thickening of the dilatant fluid caused by the pressure force introduced into the dilatant fluid via the tension body and the compression body. If the compression body presses onto the dilatant fluid in the second chamber in consequence of a sudden movement and if the force acting on the dilatant fluid reaches a predetermined threshold, the dilatant fluid undergoes a shear thickening. In this shear thickened state the dilatant fluid in the second chamber behaves incompressible, so that the compression body cannot continue to displace the dilatant fluid through the passage and cannot continue to move toward the second end of the receptacle body. Accordingly, the incompressible behavior of the dilatant fluid leads to a movement limitation of the components of the device, which in turn leads to a movement limitation of the corresponding body parts of the user.

Since the movement limitation of the device is caused by the incompressible behavior of the dilatant fluid at pressure forces, which are based on non-physiological movements, a relatively small dimensioning of the device is possible. In order to realize the desired effect of the movement limitation, especially comparatively large shear surfaces as in terms of a device having a mode of action that is purely based on shear are not necessary.

The first chamber is formed by the area between the compression body and the first end of the receptacle device and the second chamber is formed between the compression body and the second end of the receptacle device. If the compression body moves relatively to the receptacle body through the dilatant fluid as a result of a force applied via the tension body, which is less than the predetermined threshold value, the displaced dilatant fluid can flow from one chamber into the other chamber. Thereby, the dilatant fluid flows from the second chamber into the first chamber, if the compression body moves toward the second end of the receptacle device, and from the first chamber into the second chamber, if the compression body moves toward the first end of the receptacle device.

The receptacle body as well as the pull-out-body projecting out of the receptacle body each can be attached via a respective bracket to corresponding parts of the body of the user.

By means of the passage the dilatant fluid displaced by the compression body can flow from one chamber to the other chamber. The passage may be provided in a manner encircling the compression body, in which the compression body has a smaller cross-sectional area. E.g., the outer diameter of the compression body can be carried out smaller than the inner diameter of the receptacle body. Alternatively, the passage may be provided in the form of a groove in the compression body.

In a further embodiment the compression body and the dilatant fluid are operatively connected together so that in the case of a force acting on the compression body below a predetermined threshold the compression body can displace the dilatant fluid, wherein the dilatant fluid may flow relative to the compression body within the receptacle body, and in case of a force greater than or equal to the predetermined threshold acting on the compression body the compression body can press onto the dilatant fluid, wherein the dilatant fluid compressed by the compression body has the characteristics of a solid body, and wherein a flow of the dilatant fluid relative to the compression body is suppressed.

The threshold, which sets the force at which the device does not allow any more relative movement between the receptacle body and the compression body can be set for specific applications.

Thereby, the threshold value can be adjusted via the dimensioning of the device and via the nature of the dilatant fluid. As a general rule, the threshold relates to the area in a force-deflection graph of the device, in which a dilatancy step is recorded.

In a further embodiment the compression body has at least one flow channel, wherein the flow channel connects the first chamber with the second chamber fluid-technically. By means of the number and size of the flow channels, it is possible to set the predetermined threshold. The provision of flow channels in the compression body allows a delay of shear thickening and thus solidification with respect to the size of the applied force. Thus, a modification of the apparatus with respect to the threshold value is possible by means of the number and dimensioning of the flow channels in the compression body.

In a further embodiment the cross section of the receptacle body in the region of an end portion of the receptacle body tapers towards the second end of the receptacle body, wherein the compression body can be pulled in the direction of the second end of the receptacle body by means of the tension body.

Thus, it is possible that the effect of shear thickening with respect to the size of the applied force starts the sooner, the closer the compression body is located at the second end. Thus, a device with a variable threshold can be provided, wherein the threshold depends on the size of the cross section of the receptacle body. The threshold value above which the effect of the shear thickening begins is the smaller, the smaller the cross-sectional area of the receptacle body is at the corresponding position of the compression body.

In a further embodiment the compression body is tapered, wherein the taper apex is directed towards the first end of the receptacle body. This favors the returning of the compression body into a starting position. For returning the compression body into the starting position, e.g., an elastic return element can be arranged in the receptacle device, which connects the first end of the receptacle device with the compression body. If the compression body is deflected from the initial position and moved toward the second end by the tension body due to an applied force, the return element is stretched. If the force acting on the compression body is reduced or if this force ceases, the elastic return element moves the compression body back to its starting position. The tapered design of the compression body thus favors the sliding of the compression body through the dilatant fluid towards the first end of the receptacle body.

In a further embodiment the compression body has at least one projection member for increasing the compression surface of the compression body, wherein the projection member is connected via a joint with the compression body. This allows a varying threshold value and thus a varying damping effect of the device when pressing the shear body into the receptacle body. The at least one projection member is disposed adjacent to the compression body in a starting position. If the compression body is moved towards the second end of the receptacle body due to the application of a force by the tension body, and if the compression body exceeds a predetermined relative speed with respect to the flowing dilatant fluid, the at least one projection member moves out of a starting position, so that the compression surface, by means of which the compression body presses onto the dilatant fluid is increased compared to the compression surface, wherein the at least one projection member is in the starting position.

Furthermore, the at least one projection member is disposed on the compression body, so that in case of a return movement of the compression body in the direction of the first end of the receptacle body the at least one projection member returns to its starting position. The return movement can be favored by the flow of the dilatant fluid.

In a further embodiment, at the second end the receptacle body has a sealing body for sealing the interior of the receptacle body against the environment, wherein the sealing body comprises an opening for receiving the tension body, and wherein the diameter of the opening is adjustable.

Thus, the properties of the shear thickening can be influenced additionally. In particular, the ease of operation of the device, i.e., the ease of operation with which the tension body moves relatively to the opening in the sealing body is adjustable. The greater the diameter of the opening is, the smoother the compression body can move relative to the receptacle body.

Vice versa, this means that the smaller the diameter of the opening is, the more cumbersome the compression body moves relative to the receptacle body. Accordingly, it is possible to adapt the intensity with which the device intervenes in a movement of a body part to be stabilized application specifically. For example, with the progress of a healing process of a body portion that is to be stabilized the diameter of the opening may be increased gradually, so that the device permits more and more extensive movements of the body part. Furthermore, the adjustability of the diameter of the opening also can be adjusted to be adapted to the corresponding body part to be stabilized and to the user's size and weight.

The adjustability of the diameter of the opening can be realized, for example, via a slide. Alternatively, seals with differently sized apertures can be provided, wherein depending on the application, a seal with a suitable opening can be inserted into the receptacle body.

In a further embodiment the tension body is fibrous. Thus, the device can be dimensioned relatively small in size. For example, the tension body can be formed of a synthetic fiber. Such a tension body requires relatively little space and can be disposed on the user's body in a flat manner. This is particularly advantageous for applications in the field of sports, in which the device is to be designed as flat as possible and as small as possible in order to avoid the hindrance of the user or third persons.

Known synthetic fibers have strength properties which meet the requirements of the device, in particular, the stabilization of body joints, muscles and tendons.

Furthermore, a fibrous tension body enables a more flexible configuration of the device. In particular, during movements of the body part to be stabilized in the physiological range in which the force acting on the compression body is below a predetermined threshold value, the fibrous tension body allows more freedom of movement than a comparable rigid tension body. In a further embodiment the receptacle body is of a flexible form. The receptacle body may comprise a plastic or elastic material which allows an adaptation of the receptacle body to the body part to be stabilized. If the receptacle body is mounted, e.g., in the region of the ankle of the user, the receptacle body can be adapted to the contour of the ankle due to its flexible properties. The receptacle body then may be fixed to the body part in a form adapted to the corresponding body part by means of appropriate fasteners.

The flexible receptacle body has the further advantage that it can adapt to any possible flexing of the body part to be stabilized. Accordingly, the receptacle body is able to reproduce a bending movement of the body part to be stabilized. Thus, it can be ensured that the device lies flat on the body part in different positions of the body part to be stabilized. Furthermore, by means of a flexible configuration of the receptacle body a massage effect can be used. If the compression body moves relative to the receptacle body in a physiological range, i.e., when a force acting on the compression body is below the predetermined threshold value, at the location of the receiving body, on which the compression body is located a pressure can be applied to the body part of the user adjacent to the device. By means of the movement of the compression body relative to the flexible receptacle body, the applied pressure position applied to the adjacent body part by means of the device moves also. Accordingly, the adjacent body part of the user can be massaged by means of the movement of the compression body. Accordingly, the device can be used, e.g., for lymph drainage.

In a further embodiment, the receptacle body has a curved shape which is adapted to a body joint, muscle or tendon. Accordingly, the apparatus may be formed for specific applications. For example, the receptacle body can be bent around an ankle of the user. Thus, it is possible to adapt the device to the surface of a body part that is to be stabilized. In particular, due to a bent configuration of the receptacle body, the projection of the device from the body surface of the user can be reduced.

In a further embodiment the receptacle body has a width or a maximum diameter of 15 mm. Thus, the device can be dimensioned relatively small, which makes it particularly suitable for use in sports.

In a further embodiment solids are provided within the receptacle body, wherein the solids are mixed with the dilatant fluid. By means of the solids the properties of the shear thickening fluid can be influenced. In particular, the incompressible behavior of the dilatant fluid in the case of a pressure force originating from the compression body, which is equal to or greater than the predetermined threshold, can be increased through the addition of solids.

In a further embodiment, the receptacle body is a hollow fiber. This makes it possible to integrate the device in textile products such as bandages, pads, gloves, shoes and the like. The operating principle on which the device is based, allows a particularly compact design. Integrated into a hollow fiber, a device for limiting movement is possible, which is particularly suitable for the sports sector.

The aforementioned object is also achieved by a system according to the features of claim 14. Accordingly, a system is provided, which comprises a plurality of the devices as described above, wherein the receptacle bodies are arranged substantially parallel to each other.

This makes it possible, to stabilize parts of the body sufficiently, despite the relatively small dimensions of the individual devices. The forces acting on the system can be distributed in a cascading manner over the plurality of the devices.

A plurality of relatively small-sized devices enables a flat design, so that the system does not project far from the body part to be stabilized.

In a further embodiment, the plurality of devices is surrounded by an elastic sheath, wherein the elastic sheath is fluid-tight. The elastic sheath enables a massaging effect of the body part on which the system rests. Furthermore, the system can be adapted to the shape of the part of the body that is to be stabilized. Due to the fluid-tight sheath less stringent requirements are imposed on the sealing of the individual devices. Thus, the fluid-tight sheath ensures that the user does not come into contact with the dilatant fluid.

In a further embodiment, the system comprising the plurality of devices includes an at least partially circumferential flange. The flange facilitates the attachment of the system to the user's body. Thus the flange can be affixed, e.g., directly on the user's body. Alternatively, the flange can be taped to the body of the user. Furthermore, the flange can be attached to the user's body by means of a retaining element, such as a rubber band, a clip, and the like.

The partial circumferential configuration of the flange allows an adequate application of force from the adjacent body parts of the user into the system consisting of a plurality of devices. In a further embodiment a system comprises a plurality of the devices as described above, wherein the devices are being connected in series. This allows distributing the power originating from the user among several devices. Thus, a significantly smaller design of the individual devices is possible.

BRIEF DESCRIPTION OF THE DRAWINGS

Preferred further embodiments and aspects of the present invention are explained further by the following description of the figures.

FIG. 1b shows schematically a sectional view of the device of FIG. 1a, in a state in which the dilatant fluid behaves incompressible.

DETAILED DESCRIPTION OF EMBODIMENTS

Figure 1A:
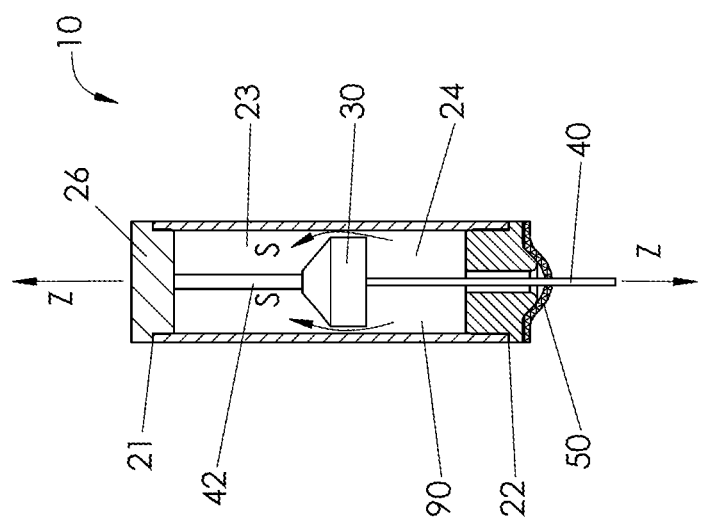
FIG. 1a shows schematically a sectional view of a device for stabilizing body joints, muscles and tendons in a state in which a dilatant fluid may flow relative to a compression body.

Hereinafter, preferred embodiments are described by means of the Figures. Thereby, the same elements, similar elements, or elements with the same effect are indicated by identical reference signs. To avoid redundancies the following description partially goes without a repeated description of these elements FIGS. 1a and 1b show a device 10 for stabilizing body joints, muscles and tendons. The device 10 comprises a receptacle body 20, which extends from a first end 21 towards a second end 22. The receptacle body 20 is filled with a dilatant fluid 90. In the receptacle body 20 a compression body 30 is disposed which divides the inner space of the receptacle body 20 into a first chamber 23 and a second chamber 24. At the compression body 30 a tension body 40 is attached, which runs longitudinally through the second chamber 24 and emerges from the receptacle body 20 at the second end 22 of the latter. The free end of the tension body 40 shown in FIGS. 1a and 1b can be connected to a body part of a user to transmit a tensile force originating from the body portion to the compression body 30 via the tension body 40.

The tension body 40 is configured in a fibrous form and can only transmit tensile forces. The tension body 40 shown in FIGS. 1a and 1b is formed of a plastic fiber. Alternatively, the tension body can comprise natural fibers or other commonly used fiber materials.

The receptacle body 20 is closed in the area of the first end 21 by means of a closure 26 so that dilatant fluid located in the receptacle body 20 can be retained in the receptacle body 20. The closure 26 is connected to the compression body 30 over a return element 42. The return element 42 is resilient and able to force the compression body 30 back into a starting position within the receptacle body 20 after a deflection has occurred by means of the tension body 40.

In the area of the second end 22 of the receptacle body 20, a sealing body 50 is arranged which seals the interior of the receptacle body 20 against the tension body 40. The sealing body 50 has an opening 52 through which the tension body 40 emerges from the interior of the receptacle body 20.

The compression body 30 can be moved through the dilatant fluid towards the second end 22 by means of the tension body 40. The receptacle body 20 is connected to a first body part and the tension body 40 is connected to a second body part, wherein the first body part and second body part can move relative to each other. The device 10 can be dimensioned specific to the application so that the device 10 allows physiological movements of the user. If, in a physiological movement, the compression body 30 is moved by means of the tension body 40 towards the second end 22, dilatant fluid 90 can flow from the second chamber 24 to the first chamber 23 through a circumferential gap between the receptacle body 20 and the compression body 30, as shown in FIG. 1a. The arrows represent the flow direction S of the dilatant fluid. If the force no longer acts on compression body 30 via the tension body 40, the compression body 30 can be moved back to the starting position by means of the return element 42, whereby the dilatant fluid flows from the first chamber 23 into the second chamber 24 through the circumferential gap between the receptacle body 20 and the compression body 30.

This behavior of the device 10 occurs when forces act on the compression body 30 that do not exceed a predetermined threshold value. The threshold value can be influenced by the dimensioning of the device 10, the composition of the dilatant fluid 90, the size of the opening 52, the size of the gap between the receptacle body 20 and the compression body 30, and the like.

If, as shown in FIG. 1b, a non-physiological force which is equal to or greater than the predetermined threshold, is applied to the compression body 30 via the tension body 40, the pressure force applied to the dilatant fluid by means of the compression body 30 leads to a shear thickening of the dilatant fluid 90 located in the second chamber 24. The dilatant fluid 90 located in the second chamber 24 briefly has a solid character, so that the dilatant fluid 90 located in the second chamber 24 behaves like a rigid body. The solid state of the dilatant fluid 90 located in the second chamber 24 blocks any further movement of the compression body 30 towards the second end 22 of the receptacle body 20. Accordingly, the two body parts connected via the device 10 are limited in their movement relative to each other. Furthermore, also a flow of dilatant fluid from the second chamber 24 towards the first chamber 23 through the gap between the receptacle body 20 and the compression body 30 is suppressed.

The compression body 30 shown in FIGS. 1a and 1b has a flat compression surface that runs substantially perpendicular to a pulling direction Z. The compression surface defines a portion of an inner surface of the second chamber 24. The pressure force that leads to the solidification of the dilatant fluid 90 in the second chamber 24, as shown in FIG. 1b, is transmitted from the compression surface to the dilatant fluid 90.

Moreover, the compression body 30 as shown in FIGS. 1a and 1b has a tapered side, which faces the first end 21. The tapered shape of the compression body 30 facilitates the return of the compression body 30 into the starting position. Accordingly, the tapered surface of the compression body 30 favors a movement through the dilatant fluid 90 towards the first end 21.

Figure 2A:
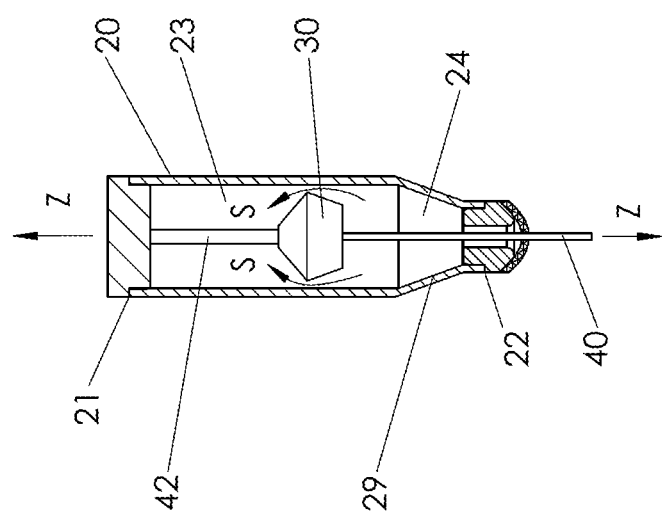
FIG. 2a shows schematically a sectional view of a device for stabilizing body joints, muscles and tendons with a tapered receptacle body in a state in which the compression body can move relative to the receptacle body.
Figure 2B:
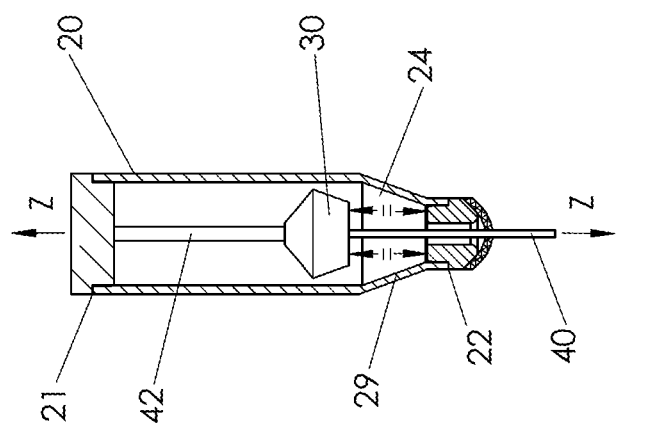
FIG. 2b shows schematically a sectional view of the device of FIG. 2a, in a state in which the compression body cannot be moved relative to the receiving body.

FIGS. 2a and 2b differ from FIGS. 1a and 1b, in that the receiving body 20 has a tapered end portion 29 in the region of the second end 22. The lateral surface of the compression body 30 extends such that it is aligned parallel to the end portion 29 of the receiving body 20.

Thereby, the damping effect of the device 10 can be reinforced continuously. The closer the compression body 30 is at the second end 22 when it undergoes a non-physiological movement, the smaller is the predetermined threshold value at which a shear thickening of the dilatant fluid 90 occurs in the second chamber 24.

The tapered end portion 29 also affects the behavior of the device 10 at physiological movements which act on the compression body 30 via the tension body 40. Thus, in the region above the end portion 29 the compression body 30 can move relatively smoothly through the dilatant fluid 90. If, however, the compression body 30 moves towards the second end 22 in the area of the tapered end portion 29, the flow resistance which the compression body 30 undergoes due to the dilatant fluid 90 increases with a decrease in the distance between the compression body 30 and the second end 22.

Figure 3A:
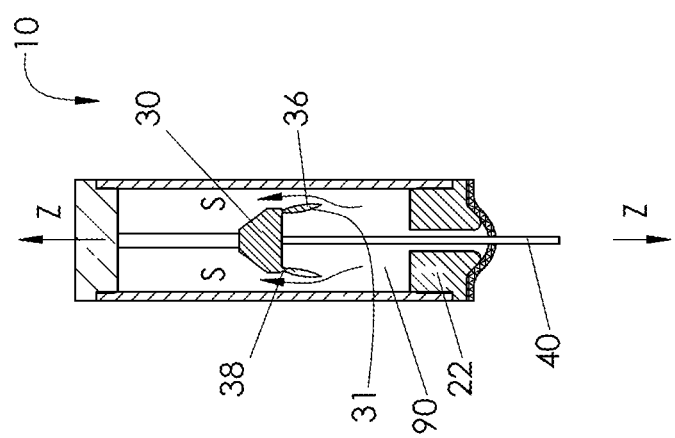
FIGS. 3a and 3b show schematically a sectional view of a device for stabilizing body joints, muscles and tendons, wherein the compression body comprises projection members, FIGS. 4a, 4b, and 4c each show schematically a sectional view of a device for stabilizing body joints, muscles and tendons, wherein the device comprises two tension bodies.
Figure 3B:
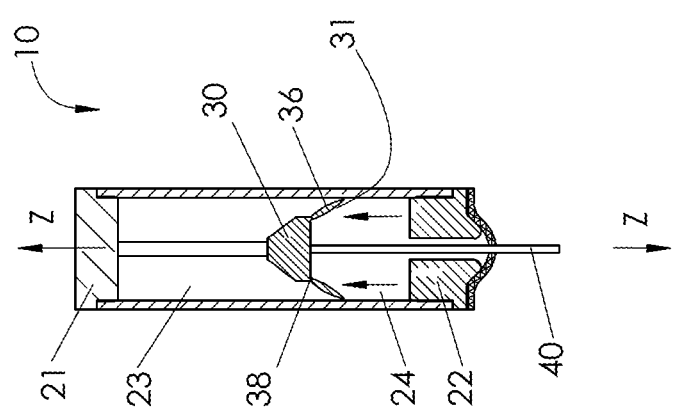

FIGS. 3a and 3b shows a device 10, which differs from the device shown in FIGS. 1a and 1b in that the compression body 30 has projection elements 36. FIG. 3a shows a compression body 30 with adjacent projection elements 36. The projection elements 36 are connected to the compression body 30 by means of joints 38.

If relatively small forces act on the tension body 40, the compression body 30 can be moved with adjacent projection elements 36 through the dilatant fluid 90 towards the second end 22. In this state the compression surface 31 of the compression body 30 acting on the dilatant fluid 90 is comparatively small.

FIG. 3b shows a compression body 30 with unfolded projection elements 36. If a non-physiological force acts on the compression body 30 via the tension member 40, the projection elements 36 are being expanded by means of dilatant fluid 90 flowing around the compression body 30. Compared to the adjacent position of the projection elements 36 shown in FIG. 3a, the compression body 30 shown in FIG. 3b has a much larger compression surface 31 with which it presses on the dilatant fluid 90 in the area of the second chamber 24. If the force acting on the compression body 30 exceeds a predetermined threshold value, a shear thickening of the dilatant fluid 90 in the second chamber 24 occurs.

Figure 4A:
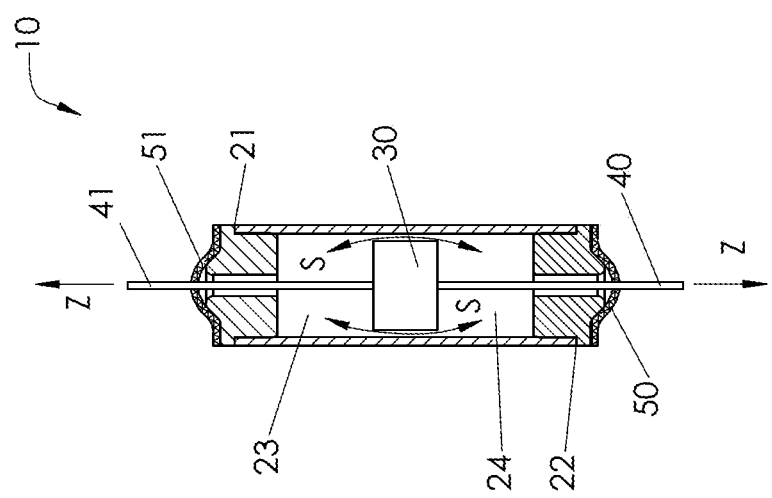
Figure 4B:
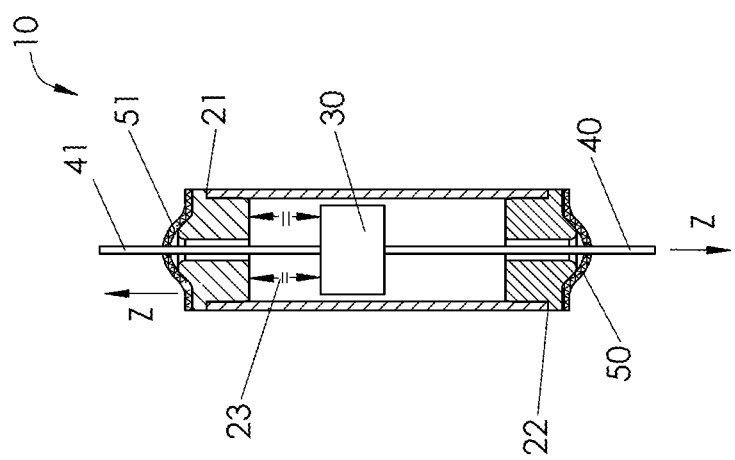
Figure 4C:
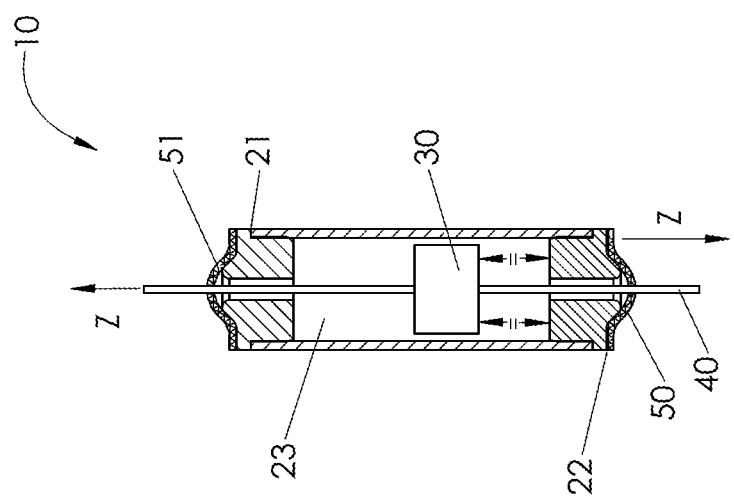

FIGS. 4a, 4b and 4c show a device 10, which can cause a shear thickening of the dilatant fluid 90 in the chamber 23 when the compression member 30 is being moved towards the first end 21, and in the chamber 24 when the compression member 30 is being moved towards the second end 22. The compression members 30 disposed in the receptacle body 20 can be pulled by a tension body 40 towards the second end 22, and by a tension body 41 towards the first end 21. If a force which results from a non-physiological movement, acts on the compression body 30 via the tension body 41 and moves the compression body 30 towards the first end 21, a shear thickening of the dilatant fluid 90 in the first chamber 23 occurs, as shown in FIG. 4b. If a force which results from a non-physiological movement, acts on the compression body 30 via the tension body 40 and moves the compression body 30 towards the second end 22, a shear thickening of the dilatant fluid 90 in the second chamber 24 occurs, as shown in FIG. 4c. In this case, the tension body 41, the receptacle body 20, and the tension body 40 are each attached to different locations on the body of the user.

Figure 5:
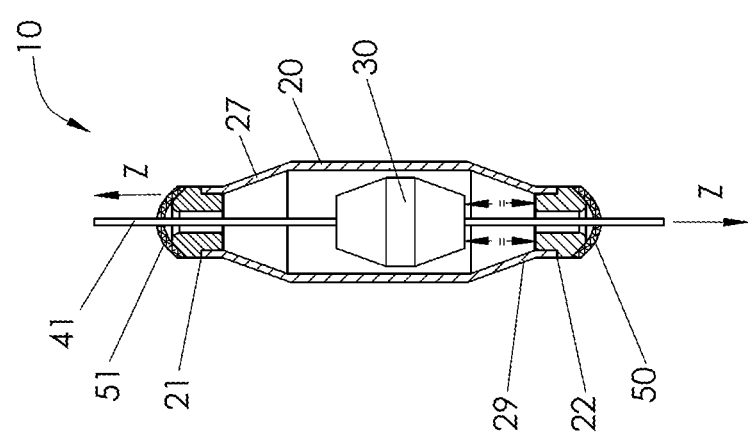
FIG. 5 shows schematically a sectional view of a device for stabilizing body joints, muscles and tendons, wherein two end portions of the receptacle body have a taper and the compression body is movable by means of two tension bodies.

FIG. 5 shows a device 10, which differs from the device shown in FIGS. 4a, 4b and 4c in that the receptacle body 20 has a tapered end portion 27 in the area of the first end 21, and a tapered end portion 29 in the area of the second end 22.

Figure 6A:
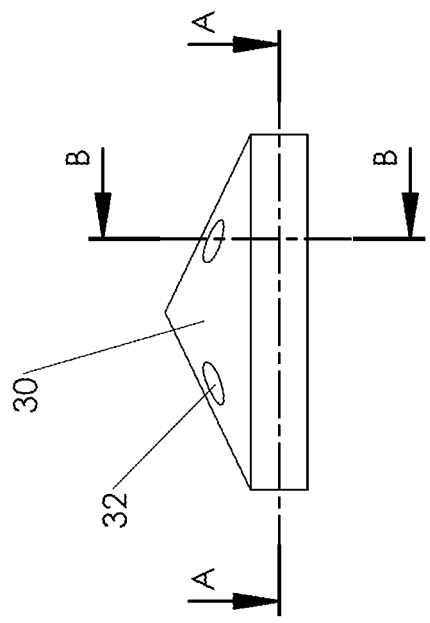
FIGS. 6a, 6b, and 6c show schematically detailed views of a compression body with flow channels.
Figure 6B:
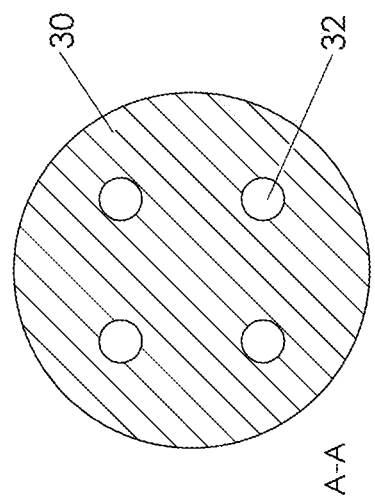
Figure 6C:
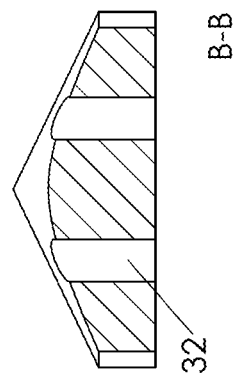
Figure 7A:
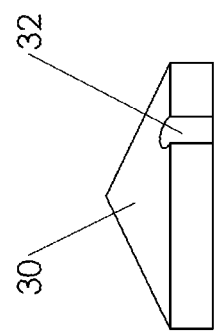
FIGS. 7a and 7b show schematically detailed views of a compression body with flow channels in the peripheral surface.
Figure 7B:
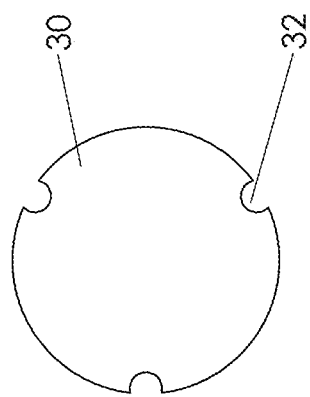

FIG. 6a shows a side view of a tapered body 30. The tapered body 30 has flow channels 32, through which dilatant fluid can flow between the first chamber and the second chamber. FIG. 6b shows a sectional view of the cutting A-A line shown in FIG. 6a. The compression body 30 comprises four flow channels 32. Alternatively, the compression body may also have one, two, three, five, six, seven or more flow channels. FIG. 6c shows a sectional view of the cutting line B-B shown in FIG. 6a. FIG. 7a shows a compression body 30 with flow channels 32 which are formed in the shape of grooves in the peripheral surface of the compression body 30. FIG. 7b shows a top view of the compression body 30. The compression body 30 has three flow channels 32.

Figure 8:
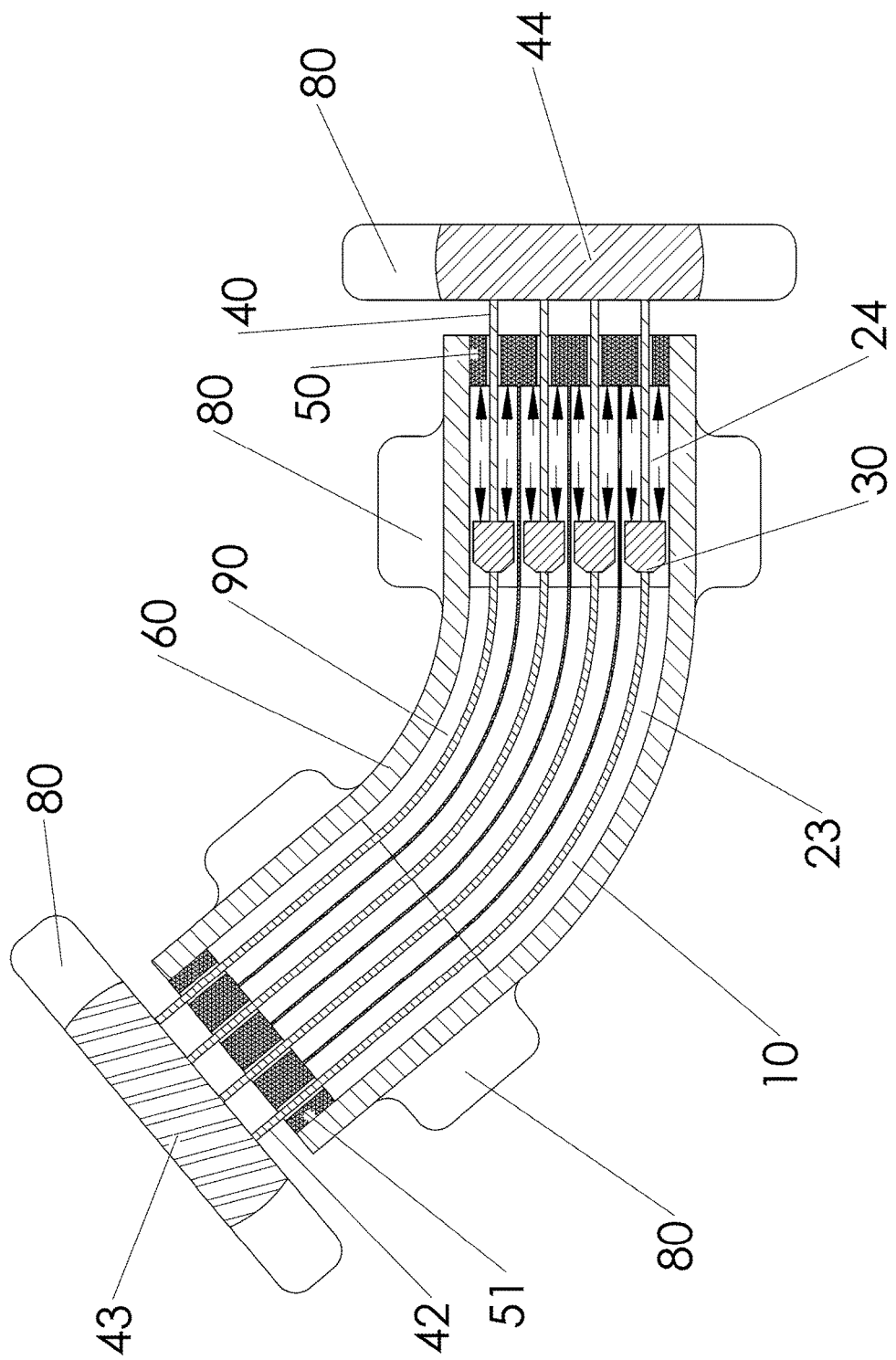
FIG. 8 shows schematically a sectional view of a pressure pad, which comprises a system consisting of a plurality of devices for stabilizing body joints, muscles and tendons.

FIG. 8 shows a system consisting of devices 10 for stabilizing body joints, muscles and tendons. In particular, four devices 10 are arranged side by side. The receptacle bodies 20 of the individual devices 10 are directly adjacent to each other and are formed in a bent manner. A compression body 30 is arranged in each of the devices 10. The compression bodies 30 divide the interior of each receptacle body 20 in a first chamber 23 and a second chamber 24. The compression bodies 30 are connected to a tension body basis 44 via tension bodies 40. Furthermore, the compression bodies 30 are connected to a return basis 43 via return elements 42. The tension bodies 40 are sealed by sealing bodies 50 against the second chambers 24. Furthermore, the return elements 42 are sealed via sealing bodies 51 against the first chambers 23.

The receptacle bodies 20 are surrounded by an elastic sheath 60. The shape of the system of devices 10 results from the elastic sheath 60. Moreover, the elastic sheath 60 ensures that the user does not come into contact with the dilatant fluid 90. Furthermore, the elastic sheath 60 can cause a massage effect, wherein the user can perceive the movement of the compression body 30 through the elastic sheath 60.

Furthermore, the elastic sheath 60 comprises flanges 80 in sections. The flanges 80 serve to attach the system of devices 10 to the user's body. For example, the flanges 80 can have an adhesive on the side facing the body of the user. By means of the adhesive the system of devices 10 can be glued directly to the user's body. Alternatively, tapes can be used to glue the flanges 80 to the user's body.

If the flanges 80 are attached to different parts of the body of the user, movements of the compression bodies 30 relative to the receptacle bodies 20 are possible. In use the individual devices 10 behave such as the device described in FIGS. 1a and 1b.

Figure 9:
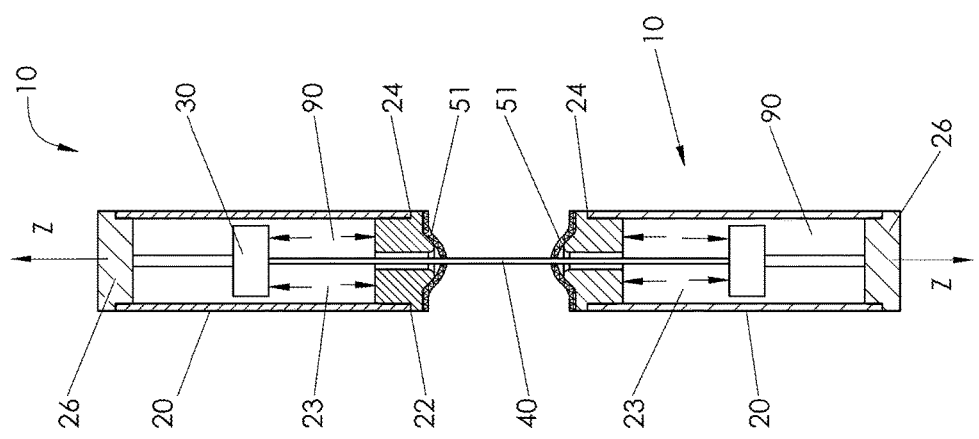
FIG. 9 shows schematically a sectional view of two devices connected in series.

FIG. 9 shows two devices 10 which are similar to the device shown in FIGS. 1a and 1b connected in series. The two devices 10 are connected via a common tension body 40. If a physiological force acts on the two receiving bodies 20 in the pulling direction Z, the receptacle bodies 20 move apart from each other. Thus, the distance between the compression bodies 30 and the second ends 22 and thus the volume of the second chambers 24 is reduced.

If a non-physiological force acts on the two receiving bodies 20 in the pulling direction Z, a solidification of the dilatant fluid 90 occurs in the second chambers 24, whereby the volume of the second chamber 23 cannot become smaller. Although, in this state forces act in the pulling direction Z the two receptacle bodies 20 cannot be moved further apart from each other.

Figure 10:
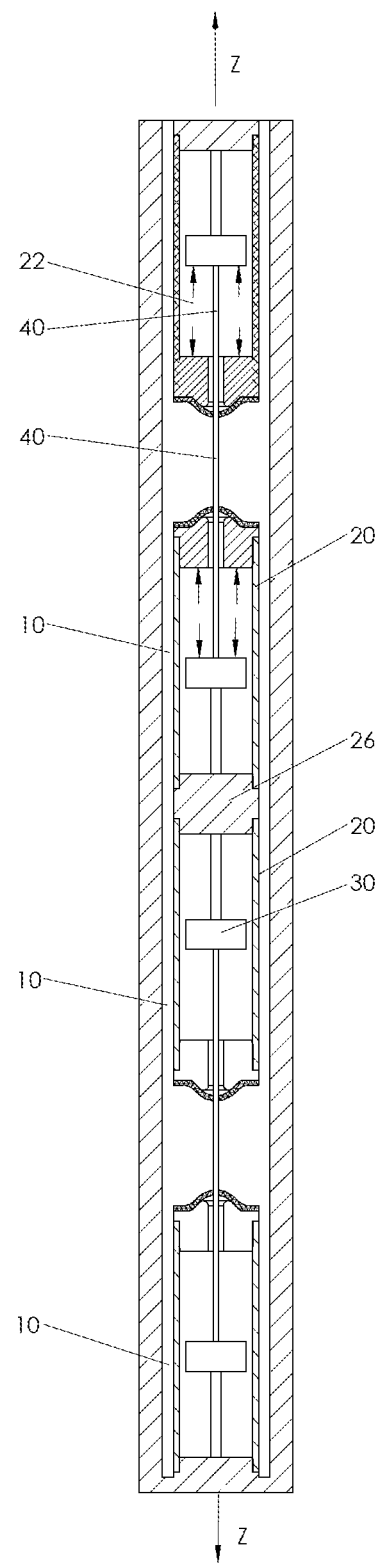
FIG. 10 shows schematically a hollow fiber in which a plurality of devices is accommodated.

FIG. 10 shows a hollow fiber 70, inside which a plurality of the devices similar to the device of FIGS. 1a and 1b are arranged. The devices 10 are connected in series in the interior of the hollow fiber 70. In this case, a device 10 shares a tension body 40 with an adjacent device 10 and shares a closure 26 with another adjacent apparatus 10. This makes it possible to integrate the device 10 in textile products such as bandages, pads, gloves, shoes and the like.

As far as applicable, all individual features which are illustrated in the various embodiments, can be combined and/or exchanged without departing from the scope of the invention.

REFERENCE SIGNS

10 Device
20 Receptacle body
21 First end
22 Second end
23 First chamber
24 Second chamber
26 Closure
29 End portion
30 Compression body
31 Compression surface
32 Flow channel
36 Projection element
40 Tension body
41 Tension body
42 Return element
43 Return basis
44 Tension body basis
50 Sealing body
51 Sealing body
52 Opening
60 Elastic sheath
70 Hollow fiber
80 Flange
90 Dilatant Fluid
S Flow direction
Z Pulling direction

The invention claimed is:

1. A device for stabilizing body joints, muscles and tendons comprising:
a receptacle body, wherein the receptacle body is filled with a dilatant fluid and the receptacle body extends in an elongated shape from a first end towards a second end, and a tension body for initiating an external force into the device,
characterized by
a compression body, wherein the compression body is arranged in the receptacle body in a relatively movable manner and is connected to the tension body, wherein the compression body divides an interior space of the receptacle body into a first chamber and a second chamber, wherein between the receptacle body and the compression body a passage is provided, wherein the passage connects the first chamber with the second chamber fluid-technically, and wherein the compression body comprises at least one compression surface which substantially defines one side of the second chamber, wherein the compression surface can press onto the dilatant fluid situated in the second chamber.

2. A system comprising a plurality of the devices according to claim 1, wherein the receptacle bodies are arranged substantially parallel to each other.

3. The system according to claim 2, wherein the plurality of devices is surrounded by means of an elastic sheath, wherein the elastic sheath is fluid-tight.

4. The system according to claim 2, wherein the plurality of devices includes a flange which is at least partially circumferential.

5. The device according to claim 1, wherein the compression body and the dilatant fluid are operatively connected together so that in the case of a force acting on the compression body below a predetermined threshold the compression body can displace the dilatant fluid, wherein the dilatant fluid may flow relative to the compression body within the receptacle body, and in case of a force greater than or equal to the predetermined threshold acting on the compression body the compression body can press onto the dilatant fluid, wherein the dilatant fluid compressed by the compression body has the characteristics of a solid body, and wherein a flow of the dilatant fluid relative to the compression body is suppressed.

6. The device according to claim 1, wherein the compression body has at least one flow channel, wherein the flow channel connects the first chamber with the second chamber fluid-technically.

7. The device according to claim 1, wherein the cross section of the receptacle body in the area of an end portion of the receptacle body tapers towards the second end of the receptacle body, wherein the compression body can be pulled in the direction of the second end of the receptacle body by means of the tension body.

8. The device according to claim 1, wherein the compression body is tapered, wherein the taper apex is directed towards the first end of the receptacle body.

9. The device according to claim 1, wherein the compression body has at least one projection member for increasing the compression surface of the compression body, wherein the projection member is connected to the compression body via a joint.

10. The device according to claim 1, wherein at the second end the receptacle body has a sealing body for sealing the interior of the receptacle body against the environment, wherein the sealing body comprises an opening for receiving the tension body, and wherein the diameter of the opening is adjustable.

11. The device according to claim 1, wherein the tension body is fibrous.

12. The device according to claim 1, wherein the receptacle body is of a flexible form.

13. The device according to claim 1, wherein the receptacle body has a curved shape which is adapted to a body joint, muscle, or tendon.

14. The device according to claim 1, wherein the receptacle body has a width or a maximum diameter of 15 mm.

15. The device according to claim 1, wherein solids are provided within the receptacle body, wherein the solids are mixed with the dilatant fluid.

16. The device according to claim 1, wherein the receptacle body is a hollow fiber.

17. A system comprising a plurality of the devices according to claim 1, wherein the devices are being connected in series.

* * * * *